United States Patent
Van Rensburg

(10) Patent No.: US 9,248,435 B2
(45) Date of Patent: Feb. 2, 2016

(54) PROCESS FOR PREPARING A COBALT-CONTAINING FISCHER TROPSCH CATALYST

(75) Inventor: Hendrik Van Rensburg, Fife (GB)

(73) Assignee: SASOL TECHNOLOGY (PROPRIETARY) LIMITED, Johannesburg (ZA)

(*) Notice: Subject to any disclaimer, the term of this patent is extended or adjusted under 35 U.S.C. 154(b) by 101 days.

(21) Appl. No.: 14/130,287

(22) PCT Filed: Aug. 31, 2012

(86) PCT No.: PCT/IB2012/054493
§ 371 (c)(1),
(2), (4) Date: Dec. 30, 2013

(87) PCT Pub. No.: WO2013/041997
PCT Pub. Date: Mar. 28, 2013

(65) Prior Publication Data
US 2014/0155501 A1  Jun. 5, 2014

(30) Foreign Application Priority Data
Sep. 21, 2011  (ZA) ................. 201106909

(51) Int. Cl.
| C07C 27/00 | (2006.01) |
| B01J 23/00 | (2006.01) |
| B01J 23/89 | (2006.01) |
| B01J 37/02 | (2006.01) |
| B01J 37/08 | (2006.01) |
| B01J 37/14 | (2006.01) |
| B01J 37/18 | (2006.01) |
| B01J 23/75 | (2006.01) |
| C07C 1/04 | (2006.01) |
| B01J 21/12 | (2006.01) |
| C10G 2/00 | (2006.01) |

(52) U.S. Cl.
CPC .............. *B01J 23/8913* (2013.01); *B01J 23/75* (2013.01); *B01J 37/024* (2013.01); *B01J 37/0205* (2013.01); *B01J 37/088* (2013.01); *B01J 37/14* (2013.01); *B01J 37/18* (2013.01); *C07C 1/043* (2013.01); *B01J 21/12* (2013.01); *B01J 37/0213* (2013.01); *C10G 2/332* (2013.01)

(58) Field of Classification Search
CPC ...... C10G 2/332; B01J 37/024; B01J 37/088; B01J 37/14; B01J 37/18; B01J 37/0205; B01J 23/75; B01J 23/8913; B01J 37/0213; B01J 21/12
USPC ......................................... 518/715; 502/325
See application file for complete search history.

(56) References Cited

U.S. PATENT DOCUMENTS

| 4,413,064 A | 11/1983 | Beuther et al. |
| 5,733,839 A | 3/1998 | Espinoza et al. |
| 6,455,462 B2 | 9/2002 | Van Berge et al. |
| 7,012,104 B2 | 3/2006 | Espinoza et al. |
| 7,524,787 B2 | 4/2009 | Visagie et al. |

FOREIGN PATENT DOCUMENTS

| CN | 101052466 A | 10/2007 |
| WO | WO0020116 | 4/2000 |
| WO | WO2008090150 A2 | 7/2008 |
| WO | 2010075516 A2 | 7/2010 |
| WO | WO2010075516 A2 | 7/2010 |
| WO | 2010097754 A2 | 9/2010 |
| WO | PCTIB2012054493 | 12/2012 |

OTHER PUBLICATIONS

Iglesia, et al., "Synthesis and Catalytic Properties of Eggshell Cobalt Catalysts for the Fischer-Tropsch Synthesis", "Journal of Catalysis 153", pp. 108-122 (1995).

*Primary Examiner* — Jafar Parsa
(74) *Attorney, Agent, or Firm* — Fellers, Snider, Blankenship, Bailey & Tippens, P.C.

(57) ABSTRACT

A process for preparing a cobalt-containing hydrocarbon synthesis catalyst includes calcining an initial catalyst precursor comprising a catalyst support supporting a cobalt compound, by heat treating the initial catalyst precursor under non-reducing conditions in order to decompose the cobalt compound and/or to cause the cobalt compound to react with oxygen, thereby to obtain a calcined initial catalyst precursor. A cobalt compound is introduced onto and/or into the calcined initial catalyst precursor so that the calcined initial catalyst precursor supports this cobalt compound thereby obtaining a subsequent catalyst precursor. The subsequent catalyst precursor is directly subjected to reduction conditions to activate the subsequent catalyst precursor, thereby to obtain a cobalt-containing hydrocarbon synthesis catalyst.

16 Claims, No Drawings

PROCESS FOR PREPARING A COBALT-CONTAINING FISCHER TROPSCH CATALYST

THIS INVENTION relates to catalysts. In particular, it relates to a process for preparing a cobalt-containing hydrocarbon synthesis catalyst, and to a process for producing hydrocarbons which includes using said hydrocarbon synthesis catalyst. The invention also relates to catalysts and products produced by the above processes.

BACKGROUND ART

It is known that supported cobalt-containing Fischer-Tropsch synthesis (FTS) catalysts can be prepared by means of impregnation of a cobalt salt onto a catalyst support coupled with drying of the impregnated support, followed by calcination of the resultant dried impregnated support, to obtain a FTS catalyst precursor. The catalyst precursor is then reduced to obtain the FTS catalyst comprising cobalt crystallites dispersed on the support.

When a cobalt compound such as cobalt nitrate is used to impregnate the catalyst support, only a relatively low cobalt loading on the catalyst support can be obtained using a single impregnation step. Accordingly, it is known to make use of multiple cobalt compound impregnation steps in order to increase the cobalt loading on the support. U.S. Pat. No. 6,455,462, U.S. Pat. No. 5,733,839 and WO 2010/075516 describe multiple impregnation methods for preparing a FTS catalyst. These methods include a first stage wherein a cobalt salt is introduced onto a catalyst support by impregnation, followed by calcination of the impregnated support. In a second stage the calcined impregnated support of the first stage is subjected to a second cobalt salt impregnation, followed by calcination. In a third stage, the calcined support of the second stage is then activated by subjecting it to a reducing gas to provide a FTS catalyst.

It is also known that in preparing a FTS catalyst the calcination step can be omitted, that is, after the catalyst support is impregnated with the cobalt salt, said impregnated support is directly reduced (without first being calcined) to provide the FTS catalyst. Such a direct reduction process is described in WO 2008/090150 and Journal of Catalysis 153 (1995) 108-122 for reducing a catalyst support which has been subjected to a single impregnation with molten cobalt nitrate.

Surprisingly, it has now been found that when a FTS catalyst is prepared according to the process of the present invention, such a catalyst demonstrates improved activity and/or lower methane selectivity over a catalyst which has been prepared according to the double impregnation procedure described above, that is where each impregnation step is followed by a calcination step, whereafter the calcined product is reduced. Surprisingly, it has also been found that the process according to the present invention provides a FTS catalyst with similar FTS activity and lower methane selectivity compared to a catalyst prepared by a double impregnation procedure wherein each impregnation step is followed by direct reduction of the impregnated catalyst support. Last-mentioned process also has the disadvantage that the product formed after the first impregnation and reduction cycle is a pyrophoric product which needs to be subjected to passivation before the second impregnation step can be carried out. This disadvantage is avoided by the present invention.

DISCLOSURE OF THE INVENTION

According to a first aspect of the present invention, there is provided a process for preparing a cobalt-containing hydrocarbon synthesis catalyst, which process includes calcining an initial catalyst precursor comprising a catalyst support supporting a cobalt compound, by heat treating the initial catalyst precursor under non-reducing conditions in order to decompose the cobalt compound and/or to cause the cobalt compound to react with oxygen, thereby to obtain a calcined initial catalyst precursor;

introducing a cobalt compound onto and/or into the calcined initial catalyst precursor so that the calcined initial catalyst precursor supports this cobalt compound thereby obtaining a subsequent catalyst precursor; and directly subjecting the subsequent catalyst precursor to reduction conditions to activate the subsequent catalyst precursor, thereby to obtain a cobalt-containing hydrocarbon synthesis catalyst.

By "non-reducing conditions" is meant conditions under which the cobalt compound is not reduced.

By 'directly subjecting the subsequent catalyst precursor to reduction conditions' is meant that the subsequent catalyst precursor is subjected to reduction conditions without first subjecting the subsequent catalyst precursor to heat treatment under oxidation conditions which causes oxidation of the supported cobalt or decomposition of the cobalt compound, i.e. without a prior calcination step. Preferably the subsequent catalyst precursor is not first subjected to heat treatment under non-reducing conditions, including oxidation conditions which causes oxidation of the supported cobalt or decomposition of the cobalt compound.

The Initial Catalyst Precursor

The process may include preparing the initial catalyst precursor by introducing the cobalt compound onto and/or into the catalyst support.

The cobalt compound introduced onto and/or into the catalyst support, or the cobalt compound supported by the catalyst support, may be any suitable organic or inorganic compound of cobalt, preferably a cobalt salt. Preferably it is an inorganic compound, more preferably an inorganic salt of cobalt. The cobalt compound may be cobalt nitrate, and particularly it may be $Co(NO_3)_2 \cdot 6H_2O$.

The cobalt compound may be introduced onto and/or into the catalyst support by any suitable manner, but preferably it is by means of impregnation. Preferably the catalyst support is impregnated by the cobalt compound by forming a mixture of the cobalt compound; a liquid carrier for the cobalt compound; and the catalyst support.

The liquid carrier may comprise a solvent for the cobalt compound and preferably the cobalt compound is dissolved in the liquid carrier.

The liquid carrier may be water.

The liquid carrier may be an acidic liquid carrier, and preferably it is an acidic aqueous composition. The acidic liquid carrier may have a pH below 5, preferably below 3, and more preferably below 3. Preferably, the pH is above 1, more preferably above 1.8.

The impregnation may be effected by any suitable impregnation method, including incipient wetness impregnation or slurry phase impregnation. Slurry phase impregnation is preferred. Preferably the cobalt compound is dissolved in the liquid carrier in order that the volume of the solution is greater than xy liter, which solution is then mixed with the catalyst support, and wherein x is the BET pore volume of the catalyst support in ml/g support, and y is the mass of catalyst support to be impregnated in kg. Preferably the volume of the solution is greater than 1.5xy liter, and preferably it is about 2xy liter.

The impregnation may be carried out at sub-atmospheric pressure, preferably below 85 kPa(a), more preferably at 30 kPa(a) and lower.

Preferably the impregnation is carried out at a temperature above 25° C. Preferably the temperature is above 40° C., more preferably it is at least 60° C., but preferably not above 95° C. Thus, the impregnation temperature can be designated $T_i$, in which case $T_i > 25°$ C., preferably $>40°$ C., more particularly 60° C.; however, preferably $T_i \leq 95°$ C.

The impregnation may be followed by partial drying of the impregnated support or the impregnation and drying may be carried out at the same time. Preferably the drying is carried out at a drying temperature above 25° C. Preferably the drying temperature is above 40° C., more preferably it is at least 60° C., but preferably not above 95° C. Thus, the drying temperature can be designated $T_{d1}$, in which case $T_{d1} > 25°$ C., preferably $>40°$ C., more preferably $\geq 60°$ C.; however, preferably, $T_{d1} \leq 95°$ C. Preferably the partial drying may be effected at sub-atmospheric conditions, more preferably below 85 kPa(a), most preferably at 30 kPa(a) and lower.

In one embodiment of the invention, the impregnation and partial drying may be carried out using a procedure which includes a first step wherein the catalyst support is impregnated (preferably slurry impregnated) with the cobalt compound at a temperature above 25° C., and at sub-atmospheric pressure, and the resultant product is dried; and at least one subsequent step wherein the resulting partially dried product of the first step is subjected to treatment at a temperature above 25° C. and at sub-atmospheric pressure, such that the temperature of the subsequent step exceeds that in the first step and/or the sub-atmospheric pressure in the subsequent step is lower than that in the first step. This two step impregnation may be the process as described in WO 00/20116, which is incorporated herein by reference.

Calcining the Initial Catalyst Precursor

As stated above, the calcination is effected in order to decompose the cobalt compound and/or to cause the cobalt compound to react with oxygen. For example, the cobalt compound (such as cobalt nitrate) may be converted into be a compound selected from CoO, CoO(OH), $Co_3O_4$, $Co_2O_3$ or a mixture of one or more thereof.

The calcination may be carried out in any suitable manner such as in a rotary kiln, a vertical furnace, or a fluidised bed reactor.

The calcination may be carried out in an inert atmosphere, but preferably it is carried out under oxidation conditions. Preferably the oxidation is carried out in the presence of oxygen, more preferably in air.

Preferably the calcination is carried out at a temperature above 95° C., more preferably above 120° C., still more preferably above 130° C., most preferably above 200° C., and preferably not above 400° C., more preferably not above 300° C. Thus, the calcination temperature can be designated $T_c$, in which case $T_c > 95°$ C., more preferably $>120°$ C., still more preferably $>130°$ C., most preferably $>200°$ C.; however, preferably, $T_c \leq 00°$ C., more preferably $\leq 300°$ C.

The calcination may be carried out by using a heating rate and an air space velocity that comply with the following criteria:
(i) when the heating rate is 1° C./min, the air space velocity is at least 0.76 $m_n^3$/(kg Co(NO$_3$)$_2$.6H$_2$O)/h; and
(ii) when the heating rate is higher than 1° C./min, the air space velocity satisfies the relation:

$$\log (\text{space velocity}) \geq \log 0.76 + \frac{\log 20 - \log 0.76}{2} \log (\text{heating rate})$$

The impregnation, the partial drying and the calcination may be repeated to achieve higher loadings of the cobalt compound on the catalyst support.

The Catalyst Support

The catalyst support may be any catalyst support suitable for supporting cobalt or a cobalt compound thereon.

The catalyst support is usually a porous support and preferably it is also pre-shaped. The support preferably has an average pore diameter between 8 and 50 nanometers, more preferably between 10 and 15 nanometers. The support pore volume may be between 0.1 and 1 ml/g catalyst support, more preferably between 0.3 and 0.9 ml/g catalyst support. The pre-shaped support may be a particulate support, preferably with an average particle size of between 1 and 500 micrometers, more preferably between 10 and 250 micrometers, still more particularly between 45 and 200 micrometers.

The catalyst support may comprise a catalyst support basis and optionally one or more modifying components. The catalyst support basis may be selected from the group consisting of alumina in the form of one or more aluminium oxides; silica ($SiO_2$); titania ($TiO_2$); magnesia (MgO); and zinc oxide (ZnO); and mixtures thereof. Preferably the support basis is selected from the group consisting of alumina in the form of one or more aluminium oxides; titania ($TiO_2$) and silica ($SiO_2$). More preferably the support basis is alumina in the form of one or more aluminium oxides. The support basis may be a commercially available product, for example Puralox (trade name) (available from Sasol Germany GmbH).

Preferably the catalyst support includes one or more modifying components. This is particularly the case where the support basis is soluble in a neutral and/or an acidic aqueous solution, or where the support basis is susceptible to hydrothermal attack as described below.

The modifying component may comprise a component that results in one or more of the following:
(i) decreasing the dissolution of the catalyst support in an aqueous environment;
(ii) suppressing the susceptibility of the catalyst support to hydrothermal attack (especially during Fischer-Tropsch synthesis);
(iii) increasing the pore volume of the catalyst support;
(iv) increasing the strength and/or attrition and/or abrasion resistance of the catalyst support.

In a preferred embodiment of the invention, the modifying component decreases the dissolution of the catalyst support in an aqueous environment and/or suppresses the susceptibility of the catalyst support to hydrothermal attack (especially during Fischer-Tropsch synthesis). Such an aqueous environment may include an aqueous acid solution and/or an aqueous neutral solution, especially such an environment encountered during an aqueous phase impregnation catalyst preparation step. Hydrothermal attack is considered to be the sintering of the catalyst support (for example aluminium oxide) during hydrocarbon synthesis, especially Fischer-Tropsch synthesis, due to exposure to high temperature and water.

The modifying component may include or consist of Si, Zr, Co, Ti, Cu, Zn, Mn, Ba, Ni, Na, K, Ca, Sn, Cr, Fe, Li, Ti, Sr, Ga, Sb, V, Hf, Th, Ce, Ge, U, Nb, Ta, W, La and mixtures of two or more thereof.

The modifying component may be selected from the group consisting of Si; Zr; Cu; Zn; Mn; Ba; La; W; Ni and mixtures of one or more thereof.

Preferably the modifying component is selected from the group consisting of Si and Zr. In a preferred embodiment of the invention, the modifying component is Si.

When the modifying component is Si, the silicon level in the resultant catalyst support may be at least 0.06 Si atoms per square nanometer of the catalyst support, preferably at least 0.13 Si atoms pre square nanometer of the catalyst support, and more preferably at least 0.26 Si atoms per square nanometer of the catalyst support.

Preferably the upper level is 2.8 Si atoms/nm$^2$ of the catalyst support.

In one preferred embodiment of the invention, the catalyst support comprises a catalyst support basis optionally including a modifying component selected from Si, Zr and W and with the catalyst support basis being selected from the group consisting of alumina in the form of one or more aluminium oxides; silica ($SiO_2$) and titania ($TiO_2$). Preferably the catalyst support basis is alumina in the form of one or more aluminium oxides and preferably it includes a modifying component which is preferably selected from Si, Zr, and W, more preferably Si. In one preferred embodiment of the invention, the catalyst support may be selected from alumina in the form of one or more aluminium oxides, silica ($SiO_2$), titania ($TiO_2$), magnesia (MgO), silica modified aluminium oxide, and mixtures thereof. Preferably the support is a silica modified aluminium oxide, for example the product obtainable under the trademark Siralox from Sasol Germany GmbH. Siralox is a spray-dried silica containing aluminium oxide support. The silica modified aluminium oxide support may be the product described in U.S. Pat. No. 5,045,519 which is incorporated herein by reference.

The one or more aluminium oxides may be selected from the group including (preferably consisting of) gamma alumina, delta alumina, theta alumina and a mixture of two or more thereof. Preferably the group includes, or, preferably, consists of gamma alumina, delta alumina and a mixture of gamma alumina and delta alumina. The aluminium oxide catalyst support may be that obtainable under the trademark Puralox, preferably Puralox SCCa 2/150 from SASOL Germany GmbH. Puralox SCCa 2/150 (trademark) is a spray-dried aluminium oxide support consisting of a mixture of gamma and delta aluminium oxide.

The aluminium oxide is preferably a crystalline compound which can be described by the formula $Al_2O_3 \cdot xH_2O$ where $0<x<1$. The term 'aluminium oxide' thus excludes $Al(OH)_3$, and AlO(OH), but includes compounds such as gamma, delta and theta alumina.

In a preferred embodiment of the invention, the catalyst support or the catalyst support basis is not a zeolite.

The Subsequent Catalyst Precursor

As stated above, the subsequent catalyst precursor is prepared by introducing the cobalt compound onto and/or into the calcined initial catalyst precursor.

The cobalt compound may be any suitable organic or inorganic compound of cobalt, preferably a cobalt salt. Preferably it is an inorganic compound, more preferably an inorganic salt of cobalt. The cobalt compound may be cobalt nitrate, and particularly it may be $Co(NO_3)_2 \cdot 6H_2O$.

Preferably the cobalt compound is the same as the cobalt compound introduced onto and/or into the catalyst support to form the initial catalyst precursor.

The cobalt compound may be introduced onto and/or into the calcined initial catalyst precursor by any suitable manner, but preferably it is by means of impregnation. Preferably the calcined initial catalyst precursor is impregnated by the cobalt compound by forming a mixture of the cobalt compound; a liquid carrier for the cobalt compound; and the calcined initial catalyst precursor.

The liquid carrier may comprise a solvent for the cobalt compound and preferably the cobalt compound is dissolved in the liquid carrier.

The liquid carrier may be water.

The liquid carrier may be an acidic liquid carrier, and preferably it is an acidic aqueous composition. The acidic liquid carrier may have a pH below 5, preferably below 3, and more preferably below 3. Preferably, the pH is above 1, more preferably above 1.8.

The impregnation may be effected by any suitable impregnation method, including incipient wetness impregnation or slurry phase impregnation. Slurry phase impregnation is preferred. Preferably the cobalt compound is dissolved in the liquid carrier in order that the volume of the solution is greater than xy liter, which solution is then mixed with the calcined initial catalyst precursor, and wherein x is the BET pore volume of the calcined initial catalyst precursor in ml/g support, and y is the mass of the calcined initial catalyst precursor to be impregnated in kg. Preferably the volume of the solution is greater than 1.5xy liter, and preferably it is about 2xy liter.

The impregnation may be carried out at sub-atmospheric pressure, preferably below 85 kPa(a), more preferably at 20 kPa(a) and lower.

Preferably the impregnation is carried out at a temperature above 25° C. Preferably the temperature is above 40° C., more preferably it is at least 60° C., but preferably not above 95° C.

The impregnation may be followed by partial drying of the impregnated support, or the impregnation and drying may be carried out at the same time. Preferably, the drying is carried out at a drying temperature above 25° C. Preferably the drying temperature is above 40° C., more preferably it is at least 60° C., but preferably not above 95° C. Thus, the drying temperature can be designated $T_{d2}$, in which case $T_{d2}>25°$ C., preferably $>40°$ C., more preferably $\geq 60°$ C.; however, preferably, $T_{d2} \leq 95°$ C. Preferably the partial drying may be effected at sub-atmospheric conditions, more preferably below 85 kPa(a), most preferably at 30 kPa(a) and lower.

In one embodiment of the invention the impregnation and partial drying may be carried out using a procedure which includes a first step wherein the calcined initial catalyst precursor is impregnated (preferably slurry impregnated) with the cobalt compound at a temperature above 25° C., and at sub-atmospheric pressure, and the resultant product is dried; and at least one subsequent step wherein the resulting partially dried product of the first step is subjected to treatment at a temperature above 25° C. and sub-atmospheric pressure, such that the temperature of the subsequent step exceeds that in the first step and/or the sub-atmospheric pressure in the subsequent step is lower than that in the first step. This two step impregnation may be the process as described in WO 00/20116, which is incorporated herein by reference.

In another embodiment of the invention, the introduction of the cobalt compound onto and/or into the calcined initial catalyst precursor may be by impregnation comprising forming a mixture of the cobalt compound, a liquid carrier for the cobalt compound, and the calcined initial catalyst precursor, coupled with drying of the resultant impregnated calcined initial catalyst precursor at a temperature above 25° C., to obtain the subsequent catalyst precursor. The drying, or partial drying, of the resultant impregnated calcined initial catalyst precursor may be effected simultaneously with and/or subsequent to the impregnation of the calcined initial catalyst precursor.

Dopant

A dopant capable of enhancing the reducibility of the active catalyst component may also be introduced onto and/or into the catalyst support and/or the calcined initial catalyst precursor. The dopant may be a metal selected from the group including palladium (Pd), platinum (Pt), ruthenium (Ru), rhenium (Re) and a mixture of one or more thereof. The mass proportion of the metal of the dopant (especially palladium metal or platinum metal) to the cobalt metal may be from 1:300 to 1:3000.

The dopant may be introduced during or after the introduction of the cobalt compound onto and/or into the catalyst support when preparing the initial catalyst precursor. Alternatively, or additionally, the dopant may be introduced during or after the introduction of the cobalt compound onto and/or into the calcined initial catalyst precursor when preparing the subsequent catalyst precursor. The dopant may be introduced as a dopant compound which is a compound of a metal selected from the group including palladium (Pd), platinum (Pt), ruthenium (Ru), rhenium (Re) and a mixture of one or more thereof. Preferably the dopant compound is an inorganic salt, and preferably it is soluble in water.

Reduction

Subjecting the subsequent catalyst precursor to reduction conditions may include contacting the subsequent catalyst precursor with a reducing gas, thereby to activate the subsequent catalyst precursor.

Subjecting the subsequent catalyst precursor to reduction conditions may include contacting the subsequent catalyst precursor with a reducing gas, thereby to activate the subsequent catalyst precursor, with the subsequent catalyst precursor being at about the drying temperature when the contacting thereof with the reducing gas is commenced.

The reducing gas may be CO or may include CO. The reducing gas may comprise, or may include, a combination of CO and $H_2$. Preferably, however, the reducing gas is hydrogen or a hydrogen containing gas. The hydrogen containing gas may consist of hydrogen and one or more inert gases which are inert in respect of the active catalyst. The hydrogen containing gas preferably contains at least 8 volume % hydrogen, preferably at least 90 volume % hydrogen.

The contacting of the reducing gas with the subsequent catalyst precursor may be effected in any suitable manner. Preferably the subsequent catalyst precursor is provided in the form of a bed of particles thereof with the reducing gas being caused to flow through the bed of particles. The bed of particles may be a fixed bed, but preferably it is a fluidised bed and preferably the reducing gas acts as the fluidising medium for the bed of catalyst precursor particles.

The reduction may be carried out at a pressure from 0.6 to 1.5 bar(a), preferably from 0.8 to 1.3 bar(a). Alternatively the pressure may be from 1.5 bar (a) to 20 bar(a). More preferably, however, the pressure is about atmospheric pressure.

The reduction is preferably carried out at a temperature in excess of 25° C. above that at which the cobalt compound and calcined cobalt compound will be reduced to an active form. Preferably the reduction is carried out at a temperature above 150° C., and preferably below 600° C. More preferably the reduction is carried out at a temperature below 500° C., most preferably below 450° C.

During activation the temperature may be varied, and preferably it is increased to a maximum temperature as set out above.

The flow of the reducing gas through the catalyst bed is preferably controlled to ensure that contaminants produced during reduction are maintained at a sufficiently low level. The reducing gas may be recycled, and preferably the recycled reducing gas is treated to remove one or more contaminants produced during reduction. The contaminants may comprise one or more of water and ammonia.

The activation may be carried out in two or more steps during which one or both of the heating rate and the space velocity of the reducing gas is varied.

During the reduction, the GHSV of the reducing gas is preferably above 1 $m_n^3$/(kg $Co(NO_3)_2.H_2O$)/hour, more preferably above 4 $m_n^3$/(kg $Co(NO_3)_2.H_2O$)/hour. Preferably the GHSV of the reducing gas is below 20 $m_n^3$/(kg $Co(NO_3)_2.H_2O$)/hour, more preferably below 15 $m_n^3$/(kg $Co(NO_3)_2.H_2O$)/hour.

During the reduction, the heating rate of the subsequent catalyst precursor is preferably above 0.1° C./min. Preferably the heating rate of the subsequent catalyst precursor is not above 1° C./min.

The Active Cobalt-Containing Hydrocarbon Synthesis Catalyst

The active cobalt-containing hydrocarbon synthesis catalyst may be a Fischer-Tropsch (FT) synthesis catalyst. The FT synthesis catalyst may be suitable for a process to be performed in a fixed bed reactor, slurry bed reactor or even a fixed fluidized bed reactor. Preferably the process is to be performed in a three phase slurry bed FT synthesis reactor.

The active cobalt-containing hydrocarbon synthesis catalyst may contain cobalt at a loading of from 5 to 70 g Co/100 g catalyst support, preferably from 20 to 40 g Co/100 g catalyst support, and more preferably from 25 to 35 g Co/100 g catalyst support.

In one preferred embodiment of the invention, the active cobalt-containing hydrocarbon synthesis catalyst is not subjected to oxidation conditions at a temperature exceeding 100° C., and is preferably not subjected to oxidation conditions at a temperature exceeding 50° C., prior to using the said catalyst in hydrocarbon synthesis.

In one embodiment of the invention, the active cobalt-containing hydrocarbon synthesis catalyst may be subjected to oxidation conditions at a temperature not exceeding 100° C., preferably at a temperature not exceeding 50° C., thereby to passify the catalyst prior to use in hydrocarbon synthesis.

In a most preferred embodiment of the invention, the active cobalt-containing hydrocarbon synthesis catalyst is not subjected to oxidation prior to using the said catalyst in hydrocarbon synthesis.

According to a second aspect of the present invention, there is provided a cobalt-containing hydrocarbon synthesis catalyst prepared according to the process of the first aspect of the invention.

Hydrocarbon Synthesis

According to a third aspect of the invention, there is provided a process for producing hydrocarbons, the process comprising preparing a cobalt-containing hydrocarbon synthesis catalyst according to the process of the first aspect of the invention; and contacting hydrogen with carbon monoxide at a temperature above 100° C. and at a pressure of at least 10 bar in the presence of the cobalt-containing hydrocarbon synthesis catalyst, thereby producing hydrocarbons and, optionally, oxygenates of hydrocarbons in a Fischer-Tropsch synthesis process.

In one preferred embodiment of the invention, the cobalt-containing hydrocarbon synthesis catalyst is not subjected to oxidation conditions above 100° C., preferably above 50° C., prior to using the said catalyst in the hydrocarbon synthesis.

In a most preferred embodiment of the invention, the cobalt-containing hydrocarbon synthesis catalyst is not subjected to oxidation prior to using the said catalyst in the hydrocarbon synthesis.

The hydrocarbon production process may also include a hydroprocessing step for converting the hydrocarbons and optionally oxygenates thereof to liquid fuels and/or chemicals.

According to a fourth aspect of the present invention, there are provided products produced by the hydrocarbon production process according to the third aspect of the invention.

The invention will now be described in more detail with reference to the following non-limiting examples.

EXAMPLES

Example 1

Comparative

HC1825 (30 g Co/0.075 g Pt/100 g $Al_2O_3$)

The catalyst is prepared via two slurry impregnations. After each of the impregnation steps the dried intermediate is heat treated/calcined in air.

First impregnation: HC1825/1 (16 g Co/0.025 g Pt/100 g $Al_2O_3$)

$Co(NO_3)_2 \cdot 6H_2O$: 23.7 g
$(NH_3)_4Pt(NO_3)_2$: 14.9 mg
Si modified Puralox: 30 g The $Co(NO_3)_2 \cdot 6H_2O$ is dissolved in 30 ml distilled water and the $(NH_3)_4Pt(NO_3)_2$ in 5 ml distilled water. Thereafter the two solutions are mixed together. The pH is adjusted to pH 2.0-2.3 using diluted $HNO_3$. The solution is stirred at 60° C. for 5-10 minutes and then the Si modified Puralox support is added to form a slurry suspension. The drying procedure below is then followed to form an initial catalyst precursor:

Drying Procedures

| Temperature (° C.) | Evaporation Pressure (kPa(a)) | Time (min) |
|---|---|---|
| 60 | No Vacuum | 10 |
| 60 | 28 | 30 |
| 75 | 28 | 90 |
| 85 | 28 | 60 |
| 85 | 5 | 180 |

After the vacuum drying, the precursor (30 g) is calcined (heat treated) in a vertical furnace in air (0.06 $m_n^3$/hour; air GHSV=4.5 $m_n^3$/(kg $Co(NO_3)_2 \cdot 6H_2O$)/h) using a temperature ramp rate of 1° C./min from room temperature (about 25° C.) to 250° C., followed by a 6 h hold time at 250° C., and thereafter cooled down to room temperature, to produce HC1825/1 (16 g Co/0.025 g Pt/100 g $Al_2O_3$), that is a calcined initial catalyst precursor.

This material is then used for the second impregnation:
$Co(NO_3)_2 \cdot 6H_2O$: 11.4 g
$(NH_3)_4Pt(NO_3)_2$: 16.3 mg
HC1825/1: 20 g The $Co(NO_3)_2 \cdot 6H_2O$ is dissolved in 20 ml distilled water and the $(NH_3)_4Pt(NO_3)_2$ in 4 ml distilled water. Thereafter the two solutions are mixed together. The pH is adjusted to pH 2.0-2.3 using diluted $HNO_3$. The solution is stirred at 60° C. for 5-10 minutes and then the calcined intermediate HC1825/1 is added and the drying procedure as described above is followed to form a subsequent catalyst precursor.

After the vacuum drying, the precursor (20 g) is calcined/heat treated in a vertical furnace in air (0.04 $m_n^3$/hour; air GHSV=5.5 $m_n^3$/(kg $Co(NO_3)_2 \cdot 6H_2O$)/h) using a temperature ramp rate of 1° C./min from room temperature (about 25° C.) to 250° C., followed by a 6 h hold time at 250° C., and thereafter cooled down to room temperature, to produce the required catalyst EXAMPLE 1 (HC1825; 30 g Co/0.075 g Pt/100 g $Al_2O_3$).

Example 2

Comparative

C1848C (30 g Co/0.05 g Pt/100 g $Al_2O_3$)

The catalyst is prepared via two slurry impregnations. After each of the impregnation steps the dried intermediate is heat treated in hydrogen.

First impregnation: C1848C11 (16 g Co/0.01 g Pt/100 g $Al_2O_3$)

$Co(NO_3)_2 \cdot 6H_2O$: 15.8 g
$(NH_3)_4Pt(NO_3)_2$: 4 mg
Si modified Puralox: 20 g The $Co(NO_3)_2 \cdot 6H_2O$ is dissolved in 20 ml distilled water and the $(NH_3)_4Pt(NO_3)_2$ in 4 ml distilled water. Thereafter the two solutions are mixed together. The pH is adjusted to pH 2.0-2.3 using diluted $HNO_3$. The solution is stirred at 60° C. for 5-10 minutes and then the Si modified Puralox support is added to form a slurry suspension. The following drying procedure is used to form an initial catalyst precursor:

Drying Procedures

| Temperature (° C.) | Evaporation Pressure (kPa(a)) | Time (min) |
|---|---|---|
| 60 | No Vacuum | 10 |
| 60 | 28 | 30 |
| 75 | 28 | 90 |
| 85 | 28 | 60 |
| 85 | 5 | 60 |
| 90 | 5 | 120 |

After the vacuum drying, the precursor (20 g) is heat treated (direct reduction) in a vertical furnace in hydrogen (100%) (0.04 $m_n^3$/hour; GHSV=4.5 $m_n^3$/(kg $Co(NO_3)_2 \cdot 6H_2O$)/h) using a temperature ramp rate of 1.0° C./min from room temperature (about 25° C.) to 425° C. (6 h hold time at 425° C.) and then cooled down to room temperature under hydrogen.

The system is purged with argon (1 h) and then treated with 1% $O_2$ (in argon) for 1 h. The temperature of the sample remains at room temperature during this passivation step. This passivation procedure is done to ensure the sample is not pyrophoric anymore and safe to handle.

This passivated material (C1848C/1) is then used for the second impregnation:
$Co(NO_3)_2 \cdot 6H_2O$: 5.7 g
$(NH_3)_4Pt(NO_3)_2$: 6.6 mg
C1848C/1: 10 g The $Co(NO_3)_2 \cdot 6H_2O$ is dissolved in 10 ml distilled water and the $(NH_3)_4Pt(NO_3)_2$ in 4 ml distilled water. Thereafter the two solutions are mixed together. The pH is adjusted to pH 2.0-2.3 using diluted $HNO_3$. The solution is stirred at 60° C. for 5-10 minutes and then the passivated C1848C/1 is added and the drying procedure as described above is followed.

After vacuum drying, the precursor (10 g) is heat treated (direct reduction) in a vertical furnace in hydrogen (100%) (0.04 $m_n^3$/hour; GHSV=11.1 $m_n^3$/(kg $Co(NO_3)_2 \cdot 6H_2O$)/h) using a temperature ramp rate of 0.5° C./min from room temperature (about 25° C.) to 425° C., followed by a 6 h hold time at 425° C., and then cooled down to room temperature under hydrogen.

The system is purged with argon (1 h) and then treated with 1% $O_2$ (in argon) for 1 h to produce the required catalyst EXAMPLE 2 (C1848C; 30 g Co/0.05 g Pt/100 g $Al_2O_3$). The temperature of the sample remains at room temperature during this passivation step. This passivation procedure is done to ensure the sample is not pyrophoric anymore and safe to handle.

Example 3

Inventive

C1846C (30 g Co/0.05 g Pt/100 g $Al_2O_3$)

The catalyst is prepared via two slurry impregnations. After the first impregnation step the dried intermediate is heat treated (calcined) in air, while after the second impregnation step the dried intermediate is heat treated (direct reduction) in hydrogen.

First impregnation: C1846C11 (16 g Co/0.01 g Pt/100 g $Al_2O_3$)
 $Co(NO_3)_2 \cdot 6H_2O$: 15.8 g
 $(NH_3)_4Pt(NO_3)_2$: 4 mg
 Si modified Puralox: 20 g The $Co(NO_3)_2 \cdot 6H_2O$ is dissolved in 20 ml distilled water and the $(NH_3)_4Pt(NO_3)_2$ in 4 ml distilled water. Thereafter the two solutions are mixed together. The pH is adjusted to pH 2.0-2.3 using diluted $HNO_3$. The solution is stirred at 60° C. for 5-10 minutes and then the Si modified Puralox support is added to form a slurry solution. The drying procedure below is followed to form an initial catalyst precursor:

Drying Procedures

| Temperature (° C.) | Evaporation Pressure (kPa(a)) | Time (min) |
|---|---|---|
| 60 | No Vacuum | 10 |
| 60 | 28 | 30 |
| 75 | 28 | 90 |
| 85 | 28 | 60 |
| 85 | 5 | 60 |
| 90 | 5 | 120 |

After the vacuum drying, the precursor (20 g) is calcined in a vertical furnace in air (0.04 $m_n^3$/hour; air GHSV=4.5 $m_n^3$/(kg $Co(NO_3)_2 \cdot 6H_2O$)/h) using a temperature ramp rate of 1° C./min from room temperature (about 25° C.) to 250° C., followed by a 6 h hold time at 250° C., and thereafter cooled down to room temperature, to produce C1846C/1 (16 g Co/0.01 g Pt/100 g $Al_2O_3$), that is a calcined initial catalyst precursor.

This material (C1846C/1) is then used for the second impregnation:
 $Co(NO_3)_2 \cdot 6H_2O$=5.7 g
 $(NH_3)_4Pt(NO_3)_2$=6.6 mg
 C1846C/1=10 g The $Co(NO_3)_2 \cdot 6H_2O$ is dissolved in 10 ml distilled water and $(NH_3)_4Pt(NO_3)_2$ in 4 ml distilled water. Thereafter the two solutions are mixed together. The pH is adjusted to pH 2.0-2.3 using diluted $HNO_3$. The solution is stirred at 60° C. for 5-10 minutes and then C1846C/1 is added and the drying procedure as described above is followed to form a subsequent catalyst precursor.

After the vacuum drying, the precursor (10 g) is heat treated (direct reduction) in a vertical furnace in hydrogen (100%) (0.04 $m_n^3$/hour; GHSV=11.1 $m_n^3$/(kg $Co(NO_3)_2 \cdot 6H_2O$)/h) using a temperature ramp rate of 0.5° C./min from room temperature (about 25° C.) to 425° C., followed by a 6 h hold time at 425° C., and then cooled down to room temperature under hydrogen.

The system is purged with argon (1 h) and then treated with 1% $O_2$ (in Argon) for 1 h to produce the required catalyst EXAMPLE 3 (C1846C; 30 g Co/0.05 g Pt/100 g $Al_2O_3$). The temperature of the sample remains at room temperature during this passivation step. This passivation procedure is done to ensure the sample is not pyrophoric anymore and safe to handle.

Example 4

Inventive

C1854A (30 g Co/0.075 g Pt/100 g $Al_2O_3$)

The catalyst is prepared via two slurry impregnations. After the first impregnation step the dried intermediate is heat treated (calcined) in air, while after the second impregnation step the dried intermediate is heat treated (direct reduction) in hydrogen.

First impregnation: C1854A/1 (16 g Co/0.025 g Pt/100 g $Al_2O_3$)
 $Co(NO_3)_2 \cdot 6H_2O$: 32 g
 $(NH_3)_4Pt(NO_3)_2$: 20 mg
 Si modified Puralox: 40 g The $Co(NO_3)_2 \cdot 6H_2O$ is dissolved in 40 ml distilled water and the $(NH_3)_4Pt(NO_3)_2$ in 8 ml distilled water. Thereafter the two solutions are mixed together The pH is adjusted to pH 2.0-2.3 using diluted $HNO_3$. The solution is stirred at 60° C. for 5-10 minutes and then the Si modified Puralox support is added to form a slurry solution. The drying procedure below is followed to form an initial catalyst precursor:

Drying Procedures

| Temperature (° C.) | Evaporation Pressure (kPa(a)) | Time (min) |
|---|---|---|
| 60 | No Vacuum | 10 |
| 60 | 28 | 30 |
| 75 | 28 | 90 |
| 85 | 28 | 60 |
| 85 | 5 | 60 |
| 90 | 5 | 120 |

After the vacuum drying, the impregnated precursor (45 g) is calcined in a vertical furnace in air (0.12 $m_n^3$/hour; air GHSV=6.0 $m_n^3$/(kg $Co(NO_3)_2 \cdot 6H_2O$)/h) using a temperature ramp rate of 1° C./min from room temperature (about 25° C.) to 250° C., followed by a 6 h hold time at 250° C., and thereafter cooled down to room temperature, to produce C1854A/1 (16 g Co/0.025 g Pt/100 g $Al_2O_3$), that is a calcined initial catalyst precursor.

This material (C1854A/1) is then used for the second impregnation:
 $Co(NO_3)_2 \cdot 6H_2O$=17.2 g
 $(NH_3)_4Pt(NO_3)_2$=25 mg
 C1854A/1=30 g The $Co(NO_3)_2 \cdot 6H_2O$ is dissolved in 30 ml distilled water and $(NH_3)_4Pt(NO_3)_2$ in 4 ml distilled water. Thereafter the two solutions are mixed together. The pH is adjusted to pH 2.0-2.3 using diluted $HNO_3$. The solution is stirred at 60° C. for 5-10 minutes and C1854A/1 is added and the drying procedure as described above is followed to form a subsequent catalyst precursor.

After the vacuum drying, the precursor (15 g) is heat treated (direct reduction) in a vertical furnace in pure hydrogen (100%) (0.06 $m_n^3$/hour; GHSV=11.0 $m_n^3$/(kg Co(NO$_3$)$_2$.6H$_2$O)/h) using a temperature ramp rate of 0.5° C./min from room temperature (about 25° C.) to 425° C., followed by a 6 h hold time at 425° C., and then cooled down to room temperature under hydrogen.

The system is purged with argon (1 h) and then treated with 1% O$_2$ (in Argon) for 1 h to produce the required catalyst EXAMPLE 4 (C1854A; 30 g Co/0.075 g Pt/100 g Al$_2$O$_3$). The temperature of the sample remains at room temperature during this passivation step. This passivation procedure is done to ensure the sample is not pyrophoric anymore and safe to handle.

Example 5

The catalyst samples of Examples 1-4 were tested for Fischer-Tropsch synthesis (FTS) performance. Prior to the FTS testing, the samples were re-reduced in hydrogen using a heating rate of 1° C./min from room temperature (about 25° C.) to 425° C., followed by a 5 h hold time at 425° C., and cooled down to 230° C.

FTS testing was done in a laboratory fixed bed reactor using 0.6 g of catalyst. FTS was done at 230° C., using a H$_2$/CO ratio of 1.6, and a pressure of 16 bar. The GHSV was constantly adjusted to maintain approximately 50% CO conversion.

The relative activity and methane selectivity for these Examples 1-4 are summarized in Table 1. The relative FTS activity is expressed relative to the performance of a (non-disclosed) reference catalyst.

TABLE 1

Relative activity and methane selectivity for Examples 1-4 during FTS testing in a laboratory fixed bed reactor, after 140 hours on line

| Catalyst | Gas during 1$^{st}$ heat treatment | Gas during 2$^{nd}$ heat treatment | Relative activity (au) | CH$_4$ (%) |
|---|---|---|---|---|
| Example 1 (comp) (HC1825) | Air | Air | 6.2 | 8.0 |
| Example 2 (comp) (C1848C) | H$_2$ | H$_2$ | 8.0 | 8.0 |
| Example 3 (inventive) (C1846C) | Air | H$_2$ | 8.2 | 7.0 |
| Example 4 (inventive) (C1854A) | Air | H$_2$ | 8.3 | 7.1 |

As can be seen from Table 1, the advantage of Examples 3 and 4 (both inventive) over Example 1, as tested in a laboratory fixed bed reactor, is an increased activity (about 30%) and a decreased methane selectivity.

Furthermore, the advantage of Examples 3 and 4 (both inventive) over Example 2 is a decreased number of process steps, as no passivation step has to be done after the first impregnation and first heat treatment steps, as well as a decreased methane selectivity.

Example 6

Inventive

C1858A (30 g Co/0.075 g Pt/100 g Al$_2$O$_3$)

This catalyst was prepared in the same manner as Example 4.

However, after the second Co/Pt impregnation and vacuum drying, the precursor (15 g) is heat treated (direct reduction) in a vertical furnace in hydrogen/nitrogen mixture (10% hydrogen) (0.06 $m_n^3$/hour; GHSV=11.0 $m_n^3$/(kg Co(NO$_3$)$_2$.6H$_2$O)/h) using a temperature ramp rate of 0.5° C./min from room temperature (about 25° C.) to 425° C., followed by a 6 h hold time at 425° C., and then cooled down to room temperature under hydrogen.

The system is purged with argon (1 h) and then treated with 1% O$_2$ (in Argon) for 1 h to produce the required catalyst EXAMPLE 6 (C1854A; 30 g Co/0.075 g Pt/100 g Al$_2$O$_3$). The temperature of the sample remains at room temperature during this passivation step. This passivation procedure is done to ensure the sample is not pyrophoric anymore and safe to handle.

Example 7

The catalyst sample of Example 6 was tested for Fischer-Tropsch synthesis (FTS) performance, in the same manner as described in Example 5.

The relative activity and methane selectivity for this Example 6 are summarized in Table 2, and compared to Example 1.

TABLE 2

Relative activity and methane selectivity for Examples 1 and 6 during FTS testing in a laboratory fixed bed reactor, after 140 hours on line.

| Catalyst | Gas during 1$^{st}$ heat treatment | Gas during 2$^{nd}$ heat treatment | Relative activity (au) | CH$_4$ (%) |
|---|---|---|---|---|
| Example 1 (comp) (HC1825) | Air | Air | 6.2 | 8.0 |
| Example 6 (inventive) (C1858A) | Air | 10% H$_2$ | 7.8 | 7.4 |

As can be seen from Table 2, the advantage of Example 6 (inventive), using a 10% hydrogen reduction gas, over Example 1, is an increased activity (about 25%) and a decreased methane selectivity.

Example 8

The catalyst samples of Examples 1 and 4 were also tested for Fischer-Tropsch synthesis (FTS) performance in a micro CSTR reactor (i.e. a slurry reactor). Prior to the FTS testing, the samples were re-reduced in hydrogen using a heating rate of 1° C./min to 425° C., followed by a 5 h hold time at 425° C., cooled down to room temperature (about 25° C.), and loaded into FTS wax to prevent oxidation.

The reduced and wax coated sample was loaded in a 1 liter micro CSTR reactor FTS using 10 g of catalyst. FTS was done at 230° C., using a H$_2$/CO ratio of 1.7, and a pressure of 18 bar. The GHSV was constantly adjusted to maintain approximately 60% CO conversion.

The relative activity and methane selectivity for these Examples 1 and 4 are summarized in Table 3. In this case relative FTS activity is expressed relative to Example 1.

TABLE 3

Relative activity and methane selectivity for Examples 1 and 4 during FTS testing in a micro CSTR reactor after 200 hours in line.

| Catalyst | Gas during 1st heat treatment | Gas during 2nd heat treatment | Relative activity (au) | $CH_4$ (%) |
|---|---|---|---|---|
| Example 1 (comp) (HC1825) | Air | Air | 1.0 | 5.9 |
| Example 4 (inventive) (C1854A) | Air | $H_2$ | 1.3 | 5.1 |

As can be seen from Table 3, the advantage of Examples 4 (inventive) over Example 1, as tested in a slurry CSTR, is again an increased activity (about 30%) and a decreased methane selectivity.

Example 9

Comparative

C1855ISAC (30 g Co/0.075 g Pt/100 g $Al_2O_3$)

The catalyst is prepared via two slurry impregnations. After the first impregnation and drying the material was calcined in air under fluidized bed conditions. After the second impregnation and drying the catalyst precursor was also calcined in air in a fixed bed followed directly with fixed bed reduction and Fischer Tropsch catalysis.

First impregnation: C1855/1 (16 g Co/0.025 g Pt/100 g $Al_2O_3$)

$Co(NO_3)_2.6H_2O$: 11.8 g
$(NH_3)_4Pt(NO_3)_2$: 7.4 mg
Si modified Puralox: 15 g The $Co(NO_3)_2.6H_2O$ is dissolved in 15 ml distilled water and the $(NH_3)_4Pt(NO_3)_2$ in 2 ml distilled water. Thereafter the two solutions are mixed together. The pH is adjusted to pH 2.0-2.3 using diluted $HNO_3$. The solution is stirred at 60° C. for 5-10 minutes and then the Si modified Puralox support is added to form a slurry suspension. The drying procedure in example 1 is then followed to form an initial catalyst precursor.

After the vacuum drying the initial catalyst precursor (15 g) is calcined (heat treated) in a vertical furnace in air (0.03 $m_n^3$/hour; air GHSV=4.5 $m_n^3$/(kg $Co(NO_3)_2.6H_2O$)/h) using a temperature ramp rate of 1° C./min from room temperature (about 25° C.) to 250° C., followed by a 6 h hold time, and cooled down to room temperature to produce C1855/1 16 g Co/0.025 g Pt/100 g $Al_2O_3$, that is a calcined initial catalyst precursor.

This material is then used for the second impregnation:
$Co(NO_3)_2.6H_2O$: 5.7 g
$(NH_3)_4Pt(NO_3)_2$: 8.1 mg
C1855/1: 10 g The $Co(NO_3)_2.6H_2O$ is dissolved in 10 ml distilled water and the $(NH_3)_4Pt(NO_3)_2$ in 2 ml distilled water. Thereafter the two solutions are mixed together. The pH is adjusted to pH 2.0-2.3 using diluted $HNO_3$. The solution is stirred at 60° C. for 5-10 minutes and then the calcined intermediate C1855/1 is added and the same drying procedure is followed to form a subsequent catalyst precursor, C1855PC/2.

After the vacuum drying the precursor, C1855PC/2 (1.0 g) is diluted with SiC (4 g, 320 grit), packed in a fixed bed reactor tube and then calcined/heat treated in air (60 ml/min) using a temperature ramp rate of 1° C./min from room temperature (about 25° C.) to 250° C., followed by a 6 h hold time, and cooled down to room temperature. After the fixed bed air calcination the sample was purged with Ar (30 min) followed by reduction in hydrogen using a heating rate of 1° C./min from room temperature (about 25° C.) to 425° C., followed by a 5 h hold time. The sample was cooled down under $H_2$ to 230° C., followed directly by FTS. FTS was done at 230° C., using a $H_2$/CO ratio of 1.6, and a pressure of 16 bar. The GHSV was constantly adjusted to maintain approximately 50% CO conversion.

Example 10

Inventive

C1855ISRC (30 g Co/0.075 g Pt/100 g $Al_2O_3$)

The vacuum dried catalyst precursor of EXAMPLE 9, C1855PC/2 (1.0 g) is diluted with SiC (4 g, 320 grit), packed in a fixed bed reactor tube and then heat treated in pure hydrogen (100 ml/min) (direct reduction) using a temperature ramp rate of 0.5° C./min from room temperature (about 25° C.) to 425° C., followed by a 6 h hold time. The sample was cooled down under $H_2$ to 230° C. followed directly by FTS. FTS was done at 230° C., using a $H_2$/CO ratio of 1.6, and a pressure of 16 bar. The GHSV was constantly adjusted to maintain approximately 50% CO conversion.

The FT-activity of Example 10 (inventive) was 20% better than the corresponding Example 9 (comparative). The methane selectivity of Example 9 and 10 was similar.

Example 11

Inventive

C1855MS (30 g Co/0.075 g Pt/100 g $Al_2O_3$)

The catalyst is prepared via two slurry impregnations. After the first impregnation step the dried intermediate is heat treated (calcined) in air, while after the second impregnation step the dried intermediate is heat treated (direct reduction) in hydrogen and unloaded into molten wax and tested for FTS in a micro CSTR slurry reactor at 230° C., using $H_2$/CO ratio of 1.7 and a pressure of 18 bar.

First impregnation: C1855MS/1 (16 g Co/0.025 g Pt/100 g $Al_2O_3$)

$Co(NO_3)_2.6H_2O$: 16 g
$(NH_3)_4Pt(NO_3)_2$: 10 mg
Si modified Puralox: 20 g

The $Co(NO_3)_2.6H_2O$ is dissolved in 20 ml distilled water and the $(NH_3)_4Pt(NO_3)_2$ in 5 ml distilled water. Thereafter the two solutions are mixed together. The pH is adjusted to pH 2.0-2.3 using diluted $HNO_3$. The solution is stirred at 60° C. for 5-10 minutes and then the Si modified Puralox support is added to form a slurry solution. The drying procedure in example 1 is followed to form an initial catalyst precursor.

After the vacuum drying the initial catalyst precursor (25 g) is calcined in a vertical furnace in air (0.07 $m_n^3$/hour; air GHSV=6.0 $m_n^3$/(kg $Co(NO_3)_2.6H_2O$)/h) using a temperature ramp rate of 1° C./min from room temperature (about 25° C.) to 250° C., followed by a 6 h hold time, and cooled down to room temperature to produce C1855MS/1, 16 g Co/0.025 g Pt/100 g $Al_2O_3$, that is a calcined initial catalyst precursor.

This material (C1855MS/1) is then used for the second impregnation:
$Co(NO_3)_2.6H_2O$=8.6 g
$(NH_3)_4Pt(NO_3)_2$=12.4 mg
C1855MS/1=15 g The $Co(NO_3)_2.6H_2O$ is dissolved in 15 ml distilled water and $(NH_3)_4Pt(NO_3)_2$ in 3 ml distilled water. Thereafter the two solutions are mixed together. The pH is adjusted to pH 2.0-2.3 using diluted $HNO_3$. The solution is stirred at 60° C. for 5-10 minutes and C1855MS/1 is added and the drying procedure as described above is followed to form a subsequent catalyst precursor.

After the vacuum drying the precursor (15 g) is heat treated (direct reduction) in a vertical furnace in pure hydrogen (100%) (0.06 $m_n^3$/hour; GHSV=11.0 $m^3{}_n$/(kg $Co(NO_3)_2.6H_2O$)/h) using a temperature ramp rate of 0.5° C./min from room temperature (about 25° C.) to 425° C., followed by a 6 h hold time, and then cooled down to room temperature (about 25° C.) under hydrogen.

The reduced catalyst is then unloaded into molten wax (25 g) and allowed to cool and solidify under a blanket of argon. The reduced and wax coated sample was loaded in a 1 liter micro CSTR reactor FTS using 10 g of catalyst. FTS was done at 230° C., using a $H_2/CO$ ratio of 1.7, and a pressure of 18 bar. The GHSV was constantly adjusted to maintain approximately 60% CO conversion.

Example 12

Comparative

Catalyst HC1825 (30 g Co/0.075 g Pt/100 g $Al_2O_3$) from EXAMPLE 1 was reduced in a vertical furnace in pure hydrogen (100%) using a temperature ramp rate of 1.0° C./min from room temperature (about 25° C.) to 425° C., followed by a 16 h hold time, and then cooled down to room temperature (about 25° C.) under hydrogen.

The reduced catalyst is then unloaded into molten wax (25 g) and allowed to cool and solidify under a blanket of argon. The reduced and wax coated sample was loaded in a 1 liter micro CSTR reactor FTS using 10 g of catalyst. FTS was done at 230° C., using a $H_2/CO$ ratio of 1.7, and a pressure of 18 bar. The GHSV was constantly adjusted to maintain approximately 60% CO conversion.

The FT-activity of catalyst Example 11 (inventive) was about 20% better than the corresponding catalyst prepared via two air calcinations (Example 12; comparative) followed by reduction, wax coating and micro slurry FTS, whilst the methane selectivity was similar (i.e. 5.9%).

After impregnation and vacuum drying, the initial or subsequent catalyst precursor is normally cooled down to room temperature (about 25° C.) before commencement of the calcination step in air or the direct reduction step in hydrogen. However, the calcination step in air or the direct reduction step in hydrogen can also be started immediately after the drying step is finished (for example at 90° C.), without cooling down to room temperature first.

The invention claimed is:

1. A process for preparing a cobalt-containing hydrocarbon synthesis catalyst, which process includes:
  (i) calcining an initial catalyst precursor comprising a catalyst support supporting a cobalt compound, by heat treating the initial catalyst precursor under non-reducing conditions in order to decompose the cobalt compound and/or to cause the cobalt compound to react with oxygen, thereby to obtain a calcined initial catalyst precursor;
  (ii) introducing a cobalt compound onto and/or into the calcined initial catalyst precursor so that the calcined initial catalyst precursor supports this cobalt compound thereby obtaining a subsequent catalyst precursor; and
  (iii) directly subjecting the subsequent catalyst precursor to reduction conditions without first subjecting it to heat treatment under oxidation conditions which cause oxidation of the supported cobalt compound or decomposition of the cobalt compound, to activate the subsequent catalyst precursor, thereby to obtain a cobalt-containing hydrocarbon synthesis catalyst.

2. The process according to claim 1, which includes preparing the initial catalyst precursor by introducing the cobalt compound onto and/or into the catalyst support.

3. The process according to claim 1, wherein the calcination of the initial catalyst precursor is carried out under oxidation conditions, at a temperature above 95° C. but not above 400° C.

4. The process according to claim 1, wherein the cobalt compound that is introduced onto and/or into the calcined initial catalyst precursor is the same as the cobalt compound of the initial catalyst precursor.

5. The process according to claim 4, wherein the cobalt compound is $Co(NO_3)_2.6H_2O$.

6. The process according to claim 1, wherein the introduction of the cobalt compound onto and/or into the calcined initial catalyst precursor is by slurry phase impregnation.

7. The process according to claim 6, wherein the slurry phase impregnation is carried out at a sub-atmospheric pressure below 85 kPa(a), and at a temperature above 25° C. but not above 95° C.

8. The process according to claim 6, wherein the slurry phase impregnation is followed by partial drying of the impregnated calcined initial catalyst precursor, at a drying temperature above 25° C. and at a sub-atmospheric pressure below 85 kPa(a).

9. The process according to claim 1, wherein subjecting the subsequent catalyst precursor to reduction conditions includes contacting the subsequent catalyst precursor with a reducing gas, thereby to activate the subsequent catalyst precursor.

10. The process according to claim 1, wherein the introduction of the cobalt compound onto and/or into the calcined initial catalyst precursor is by impregnation comprising forming a mixture of the cobalt compound, a liquid carrier for the cobalt compound, and the calcined initial catalyst precursor, and drying the resultant impregnated calcined initial catalyst precursor at a temperature above 25° C., to obtain the subsequent catalyst precursor.

11. A process according to claim 10, wherein subjecting the subsequent catalyst precursor to reduction conditions includes contacting the subsequent catalyst precursor with a reducing gas, thereby to activate the subsequent catalyst precursor, with the subsequent catalyst precursor being at about the drying temperature when the contacting thereof with the reducing gas is commenced.

12. A process according to claim 9, wherein the reducing gas is hydrogen or a hydrogen containing gas.

13. A process according to claim 9, wherein the contacting of the subsequent catalyst precursor with the reducing gas is effected by causing the reducing gas to flow through a bed of particles of the subsequent catalyst precursor.

14. A process for producing hydrocarbons, the process comprising:
  a.) preparing a cobalt-containing hydrocarbon synthesis catalyst according to a process including;
    (i) calcining an initial catalyst precursor comprising a catalyst support supporting a cobalt compound, by heat treating the initial catalyst precursor under non-reducing conditions in order to decompose the cobalt compound and/or to cause the cobalt compound to react with oxygen, thereby to obtain a calcined initial catalyst precursor;
    (ii) introducing a cobalt compound onto and/or into the calcined initial catalyst precursor so that the calcined initial catalyst precursor supports this cobalt compound thereby obtaining a subsequent catalyst precursor; and (iii) directly subjecting the subsequent catalyst precursor to reduction conditions without first subjecting it to heat treatment under oxidation conditions which cause oxidation of the supported cobalt compound or decomposition of the cobalt compound, to activate the subsequent catalyst precursor, thereby to obtain a cobalt-containing hydrocarbon synthesis catalyst; and b.) contacting hydrogen with carbon monoxide at a temperature above 100° C. and at a pressure of at least 10 bar in the presence of said cobalt-containing hydrocarbon synthesis catalyst, thereby producing hydrocarbons in a Fischer-Tropsch synthesis process.

15. A process according to claim 11, wherein the contacting of the subsequent catalyst precursor with the reducing gas is effected by causing the reducing gas to flow through a bed of particles of the subsequent catalyst precursor.

16. A process according to claim 11, wherein the reducing gas is hydrogen or a hydrogen containing gas.

* * * * *